US010743785B2

(12) United States Patent
Hu et al.

(10) Patent No.: US 10,743,785 B2
(45) Date of Patent: Aug. 18, 2020

(54) HYBRID ONE- AND TWO-SIDED FLOW-ENCODING ONLY (HOTFEO) FOR VELOCITY-ENCODING PHASE CONTRAST MRI

(71) Applicant: The Regents of the University of California, Oakland, CA (US)

(72) Inventors: Peng Hu, Los Angeles, CA (US); Da Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 376 days.

(21) Appl. No.: 15/755,041

(22) PCT Filed: Aug. 25, 2016

(86) PCT No.: PCT/US2016/048726
§ 371 (c)(1),
(2) Date: Feb. 23, 2018

(87) PCT Pub. No.: WO2017/035369
PCT Pub. Date: Mar. 2, 2017

(65) Prior Publication Data
US 2018/0235485 A1 Aug. 23, 2018

Related U.S. Application Data

(60) Provisional application No. 62/210,830, filed on Aug. 27, 2015.

(51) Int. Cl.
*A61B 5/026* (2006.01)
*G01R 33/48* (2006.01)
(Continued)

(52) U.S. Cl.
CPC ........ *A61B 5/0263* (2013.01); *G01R 33/4822* (2013.01); *G01R 33/5635* (2013.01);
(Continued)

(58) Field of Classification Search
CPC .. A61B 5/0263; A61B 5/055; G01R 33/5635; G01R 33/5673; G01R 33/56316;
(Continued)

(56) References Cited

U.S. PATENT DOCUMENTS 7,561,909 B1   7/2009 Pai
8,903,470 B2   12/2014 Yamada
(Continued)

FOREIGN PATENT DOCUMENTS

KR   20020039631   5/2002

OTHER PUBLICATIONS

Jung et al. 2012 "Phase-Contrast MRI and Flow Quantification" in "magnetic Resonance Angiography: Principles and Applications" JC Carr & TJ Carroll, Edts., Springer 2012, Chapt.3 p. 51-64 (Year: 2012).*
(Continued)

*Primary Examiner* — Jeffrey G Hoekstra
*Assistant Examiner* — Patrick M Mehl
(74) *Attorney, Agent, or Firm* — Quarles & Brady LLP

(57) ABSTRACT

A phase-contrast MRI (PC-MRI) system and method employing a Hybrid One- and Two-sided Flow Encoding Only (HOTFEO) acquisition scheme for accurate blood flow and velocity measurements of three-directional-velocity-encoding PC-MRI.

20 Claims, 10 Drawing Sheets

(51) Int. Cl.
*G01R 33/563* (2006.01)
*G01R 33/567* (2006.01)
*G01R 33/565* (2006.01)

(52) U.S. Cl.
CPC ... *G01R 33/5673* (2013.01); *G01R 33/56316* (2013.01); *G01R 33/56518* (2013.01)

(58) Field of Classification Search
CPC .......... G01R 33/4822; G01R 33/56518; G01R 33/563; A61K 49/06; G06T 2207/10088; G06T 2207/10096; G06T 2207/30104; G06T 7/00

See application file for complete search history.

(56) References Cited

U.S. PATENT DOCUMENTS

| | | |
|---|---|---|
| 2009/0105582 A1 | 4/2009 | Dougherty |
| 2009/0326367 A1 | 12/2009 | Doyle |
| 2011/0064294 A1 | 3/2011 | Abe |

OTHER PUBLICATIONS

Markl et al. 2012 J. Mag. Reson. Imag. 36:1015-1036 (Year: 2012).*
Bock J, et al. In vivo noninvasive 4D pressure difference mapping in the human aorta: Phantom comparison and application in healthy volunteers and patients. Magn Reson Med. 2011;66(4):1079-1088. doi:10.1002/mrm.22907.
Callaghan FM, et al. Use of Multi-Velocity Encoding 4D Flow MRI to Improve Quantification of Flow Patterns in the Aorta. J Magn Reson Imaging. 2016;43(2):352-363. doi:10.1002/jmri.24991.
Enzmann DR, et al. Blood flow in major cerebral arteries measured by phase-contrast cine MR. Am J Neuroradiol. 1994;15(1):123-129.
Extended European Search Report for applicatoin 16840133.9, dated Mar. 26, 2019, 8 pages.
Griswold MA, et al. Generalized autocalibrating partially parallel acquisitions (GRAPPA). Magn Reson Med. 2002;47(6):1202-1210. doi:10.1002/mrm.10171.
Gu T, et al. PC VIPR: A High-Speed 3D Phase-Contrast Method for Flow Quantification and High-Resolution Angiography. Am J Neuroradiol. 2005;26(4):743-749.
Huang F, et al. k-t GRAPPA: A k-space implementation for dynamic MRI with high reduction factor. Magn Reson Med. 2005;54(5):1172-1184. doi:10.1002/mrm.20641.
International Search Report and Written Opinion for application PCT/US2016/048726, dated Dec. 5, 2016, 9 pages.
Jung B, et al. Highly k-t-spaceaccelerated phase-contrast MRI. Magn. Reson. Med. 2008;60:1169-1177. doi: 10.1002/mrm.21764.
Kim D, et al. Accelerated phase-contrast cine MRI using k-t SPARSE-SENSE. Magn Reson Med. 2012;67(4):1054-1064. doi:10.1002/mrm.23088.
Kwak Y, et al. Accelerated aortic flow assessment with compressed sensing with and without use of the sparsity of the complex difference image. Magn Reson Med. 2013;70(3):851-858. doi:10.1002/mrm.24514.
Lin, Hung-Yu, et al. "Shared velocity encoding: a method to improve the temporal resolution of phase-contrast velocity measurements." Magnetic resonance in medicine 68.3 (2012): 703-710.
Lustig M, et al. Sparse MRI: The application of compressed sensing for rapid MR imaging. Magn Reson Med. 2007;58(6):1182-1195. doi:10.1002/mrm.21391.
Markl M, et al. 4D flow MRI. J Magn Reson Imaging. 2012;36(5):1015-1036. doi:10.1002/jmri.23632.
Markl M, et al. Reproducibility of flow and wall shear stress analysis using flow-sensitive four-dimensional MRI. J Magn Reson Imaging. 2011;33(4):988-994. doi:10.1002/jmri.22519.
Negahdar M, et al. Comparison of Cartesian, UTE radial, and spiral phase-contrast MRI in measurement of blood flow in extracranial carotid arteries: normal subjects. In: vol. 8672. ; 2013:86720A-86720A-9. doi:10.1117/12.2007438.
Pelc NJ, et al. Encoding strategies for three-direction phase-contrast MR imaging of flow. J Magn Reson Imaging. 1991;1(4):405-413. doi:10.1002/jmri.1880010404.
Pruessmann KP, et al. SENSE: Sensitivity encoding for fast MRI. Magn Reson Med. 1999;42(5):952-962. doi:10.1002/(SICI)1522-2594(199911)42:5<952::AID-MRM16>3.0.CO;2-S.
Tao Y, et al. Carotid blood flow measurement accelerated by compressed sensing: Validation in healthy volunteers. Magn Reson Imaging. 2013;31(9):1485-1491. doi:10.1016/j.mri.2013.05.009.
Thompson RB, et al. High temporal resolution phase contrast MRI with multiecho acquisitions†. Magn Reson Med. 2002;47(3):499-512. doi:10.1002/mrm.10079.
Wang D, et al, Phase-contrast MRI with hybrid one and two-sided flow encoding and velocity spectrum separation. Magn Reson Med. 2017;78(1):182-192.
Wang D, et al. 2D PC-MRI with 3D Flow Encoding acquisitions Only (FEsO) for Accurate Slice Orientation-Independent Blood Flow Measurement. In: Proceedings of 15th Annual Meeting of ISMRM, Toronto, Canada, 2015. Abstract 2737.
Wang, D, et al, "Accelerated Phase-Contrast MRI Using Hybrid One- and two-sided flow-encodings only (HOTFEO)" Proceedings of the International Society for Magnetic Resonance in Medicine, 24th Annual Meeting and Exhibition, Singapore, May 7-13, 2016, vol. 24, 2595, Apr. 22, 2016 XP040683636.
Wang, D, et al. "Hybrid One-and Two-sided Flow-Encodings Only (HOTFEO) to accelerate 4D flow MRI." Journal of Cardiovascular Magnetic Resonance 18.1 (2016): p. 364.
Wang, D, et al. "Phase contrast MRI with flow compensation view sharing." Magnetic resonance in medicine 73.2 (2015): 505-513.

* cited by examiner

HYBRID ONE- AND TWO-SIDED FLOW-ENCODING ONLY (HOTFEO) FOR VELOCITY-ENCODING PHASE CONTRAST MRI

CROSS-REFERENCE TO RELATED APPLICATIONS

This application represents the national stage entry of International Application PCT/US2016/048726 filed Aug. 25, 2016 and claims priority to U.S. Provisional Patent Application 62/210,830 filed Aug. 27, 2015. The contents of this application are hereby incorporated by reference as if set forth in their entirety herein.

STATEMENT REGARDING FEDERALLY SPONSORED RESEARCH OR DEVELOPMENT

This invention was made with Government support under 113427 awarded by the National Institutes of Health. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to imaging, and more particularly to phase-contrast (PC) MRI.

2. Background Discussion

Phase-contrast MRI (PC-MRI) has been extensively used clinically for visualization and quantification of blood flow and velocity. The conventional 2D PC-MRI alternatively acquires flow-compensated (FC) and through-plane direction (i.e. z-direction) flow-encoded (FE) data, and the blood flow velocity is encoded by the phase difference between the FC and FE data.

The FE gradients can also be applied in the two in-plane orientations, i.e. phase-encoding direction (y-direction) and readout direction (x-direction). This further development of three-directional velocity encoding PC-MRI with time resolved (CINE) three-dimensional (3D) acquisitions is also commonly referred to a 4D flow MRI. 4D flow generally allows for better visualization, more flexible retrospective territories selection and more accurate peak velocity estimation.

Since theses three-directional velocity encoding PC-MRI techniques (2D and 4D) typically acquire FC and three-directional FE data (FC/3FE) in an interleaved fashion, four acquisitions are needed to update one cardiac phase. This results in poorer temporal resolution and temporal footprint than conventional 2D through-plane FE PC-MRI. As temporal resolution and temporal footprint of PC-MRI are two important indices to determine the measurement accuracy of peak velocity, this has an impact on diagnosis of a number of clinical diseases, such as carotid artery stenosis. Low temporal resolution and long temporal footprint can result in under-estimations of peak velocities as well as pressure gradients across valves or stenoses.

While the temporal resolution and temporal footprint can be improved by reducing views-per-segment (the number of k-space lines acquired for each cardiac phase within a single cardiac cycle), this accordingly increases total imaging acquisition time. Fast MRI techniques have been developed and applied in PC-MRI to reduce the total acquisition time. However, with certain views-per-segment, these fast PC-MRI techniques can barely improve the temporal resolution and temporal footprint, which may not be significantly helpful on improving measurement accuracy of peak velocity.

View-sharing PC-MRI techniques have also been developed in attempt to improve the temporal resolution. A Shared Velocity Encoding (SVE) technique has been employed to improve temporal resolution. However, the temporal footprint of each cardiac phase in the SVE technique is the same as traditional 2D PC-MRI, and may suffer from even longer temporal footprint (6*TR*views-per-segment) than conventional 4D flow acquisition (4*TR*views-per-segment) when implemented with three-dimensional FE PC-MRI.

BRIEF SUMMARY

An aspect of the present description is a fast phase-contrast MRI (PC-MRI) system and method employing a Hybrid One- and Two-sided Flow Encoding Only (HOTFEO) acquisition scheme for accurate blood flow and velocity measurements of three-directional-velocity-encoding PC-MRI. Velocity direction constraint is used to accelerate three-directional-velocity-encoding PC-MRI by 4/3-fold using three-directional (3D) flow-encoded (FE) acquisitions to provide more accurate calculation of background FC phase without acquiring flow-compensated (FC) data, while maintaining the measurement accuracy of total volumetric flow and total maximum peak velocity measurements. The hybrid one- and two-sided FE acquisition of the present description improves calculation accuracy and addresses ill-conditions of the constraint to extend its applications with minimal limitations.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 6A:
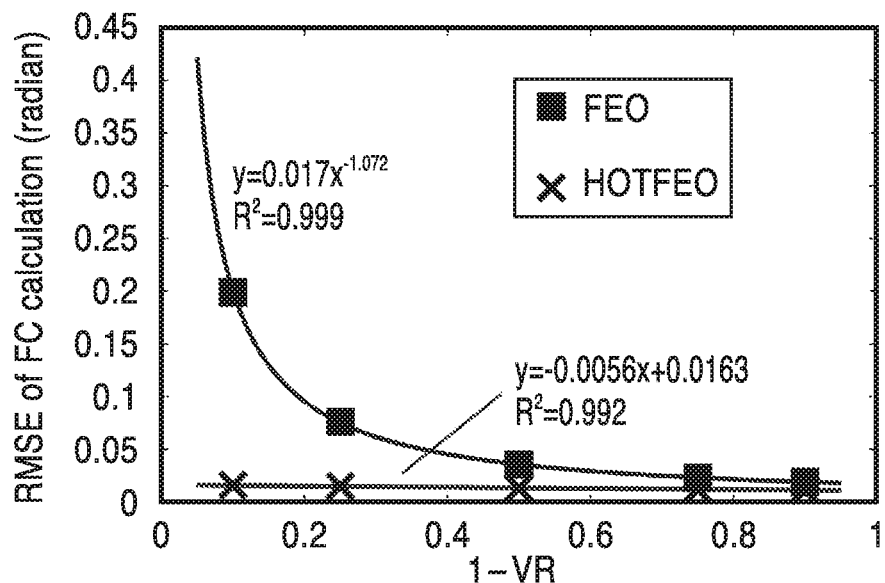

FIG. 6A is a plot showing the correlation of the RMSE of calculated FC phase and 1-VR. The two parameters have an inverse correlation of FEO, and linear correlation of HOTFEO. The FEO has larger FC estimation errors than HOTFEO, when the 1-VR closes to 0, the FEO will fail to estimate the FC phase, but the HOTFEO still provides good FC estimation.

Figure 6B:
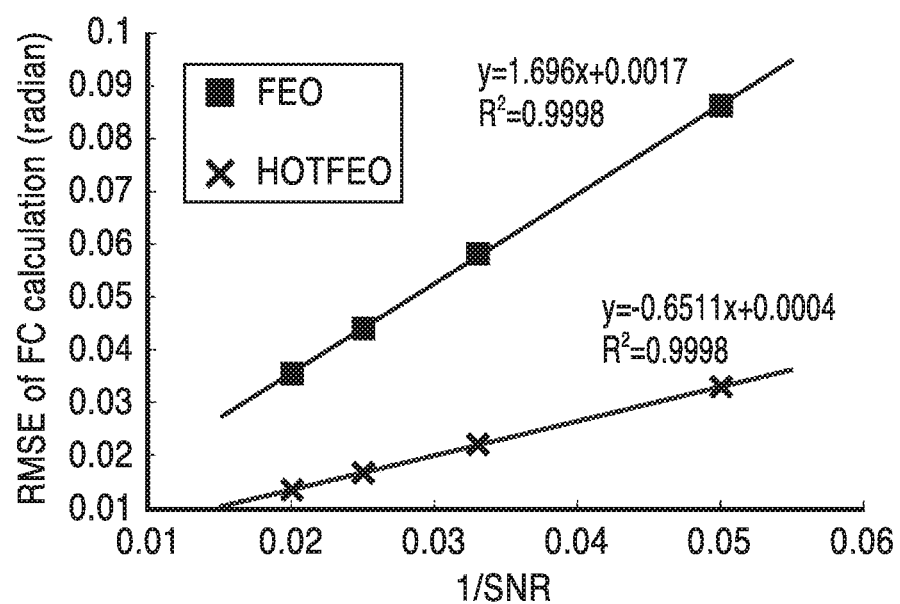

FIG. 6B is a plot showing the correlation of the RMSE of calculated FC phase and 1/SNR. The RMSE of the FC calculation has linear regression with noise level (1/SNR) for both FEO and HOTFEO. Higher SNR tends to have better FC estimation for both techniques.

Figure 7A:
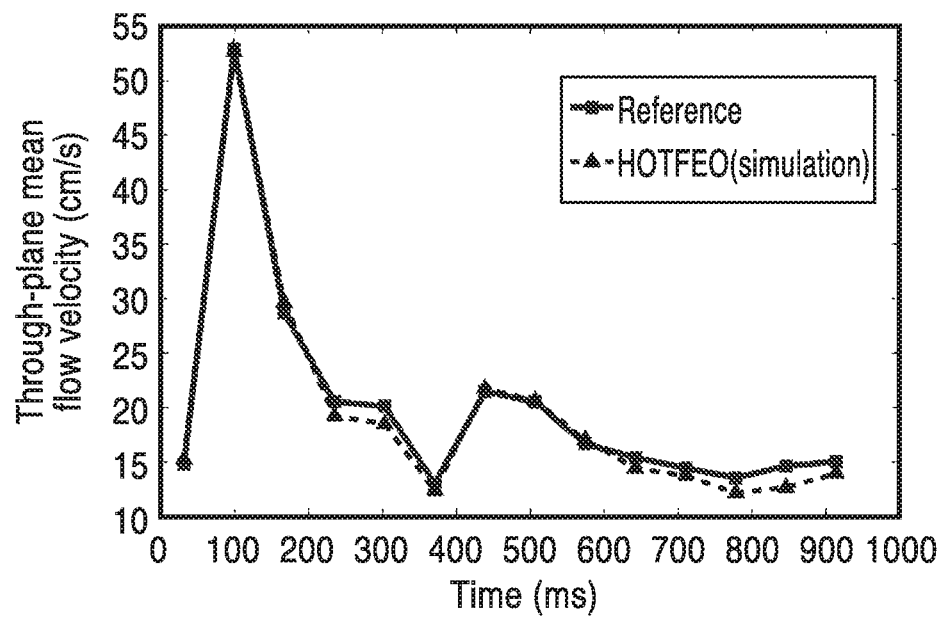

FIG. 7A is a plot of the total mean flow velocity waveforms of the reference FC/3FE PC-MRI and simulated HOTFEO.

Figure 7B:
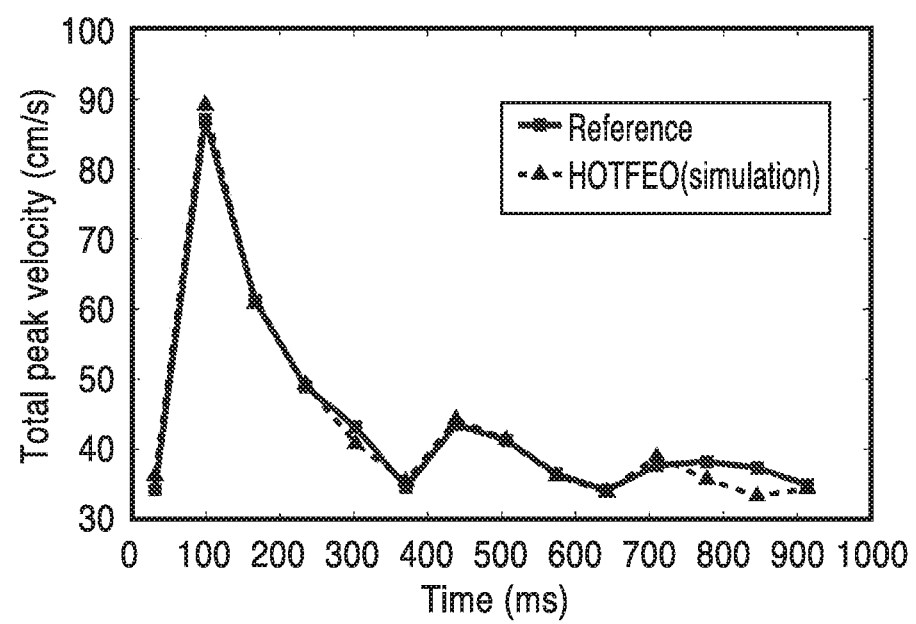

FIG. 7B is a plot of the total peak velocity waveforms of the reference FC/3FE PC-MRI and simulated HOTFEO.

Figure 8A:
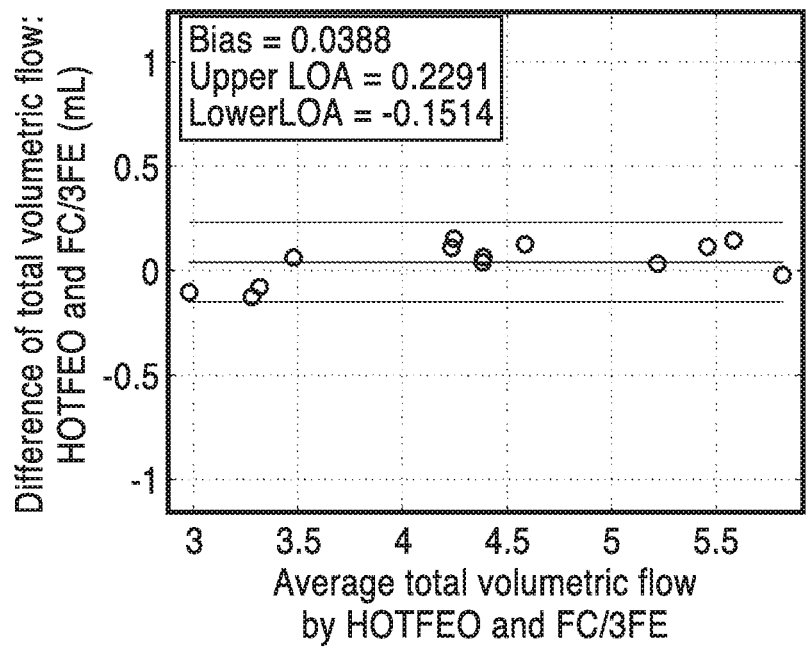

FIG. 8A shows Bland-Altman plots of total volumetric flow measurements between simulated HOTFEO and reference FC/3FE.

Figure 8B:
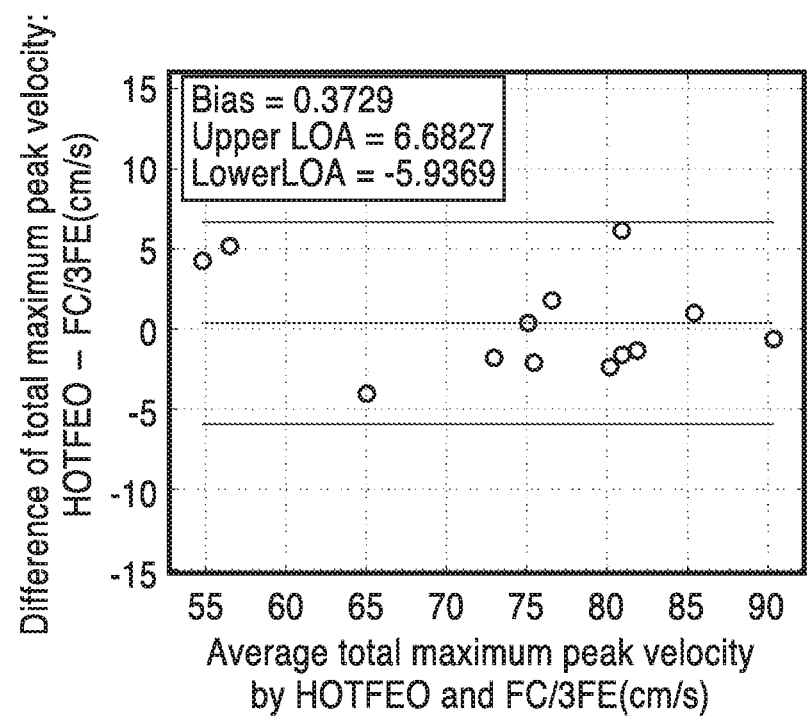

FIG. 8B shows Bland-Altman plots of total maximum peak velocity measurements between simulated HOTFEO and reference FC/3FE.

Figure 9A:
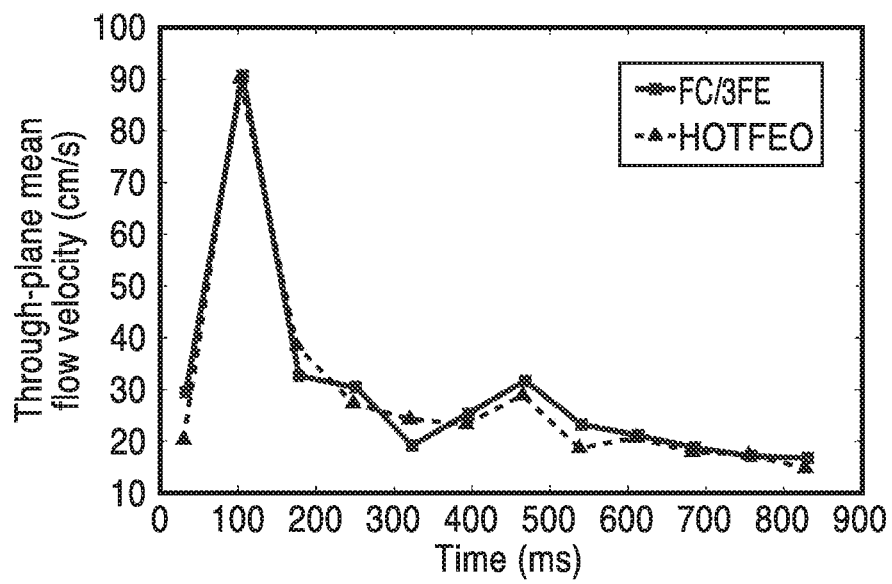

FIG. 9A shows a plot of the total mean flow velocity waveforms of 2D reference FC/3FE PC-MRI and 2D HOTFEO.

Figure 9B:
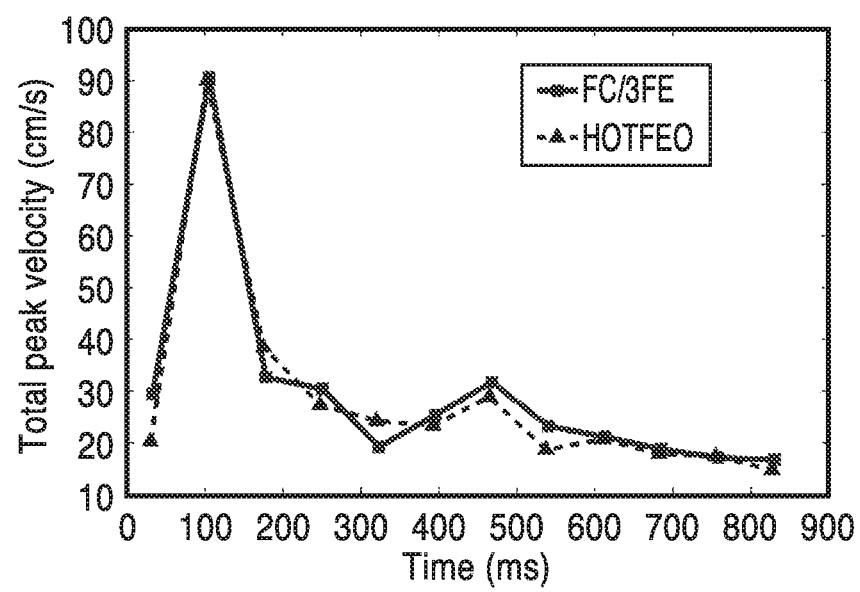

FIG. 9B shows a plot of the total peak velocity waveforms of 2D reference FC/3FE PC-MRI and 2D HOTFEO.

Figure 10A:
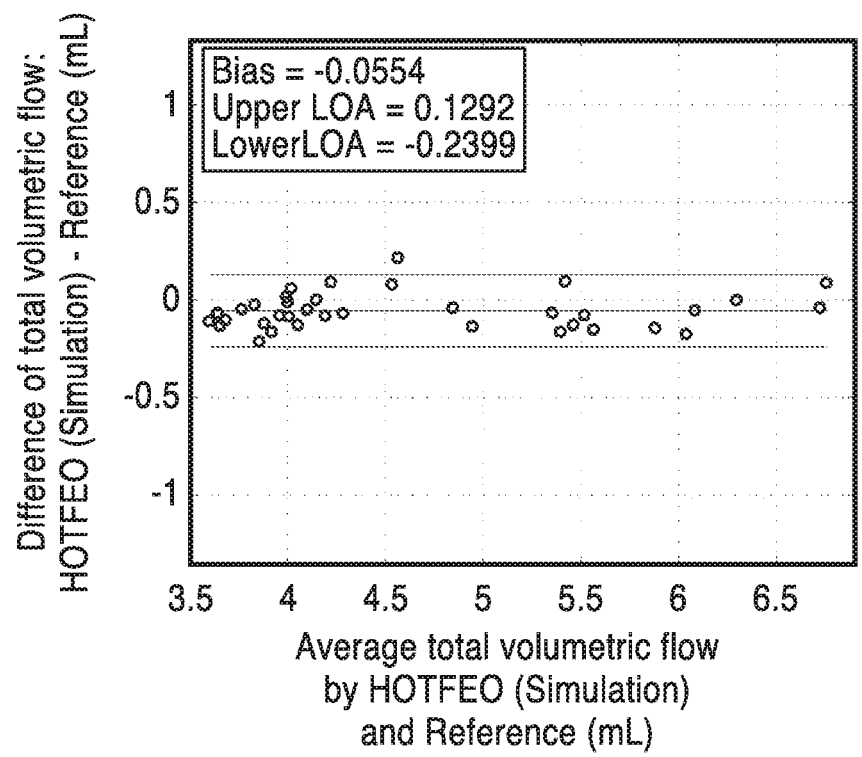

FIG. 10A shows Bland-Altman plots of total volumetric flow measurement between 2D reference FC/3FE and 2D HOTFEO.

Figure 10B:
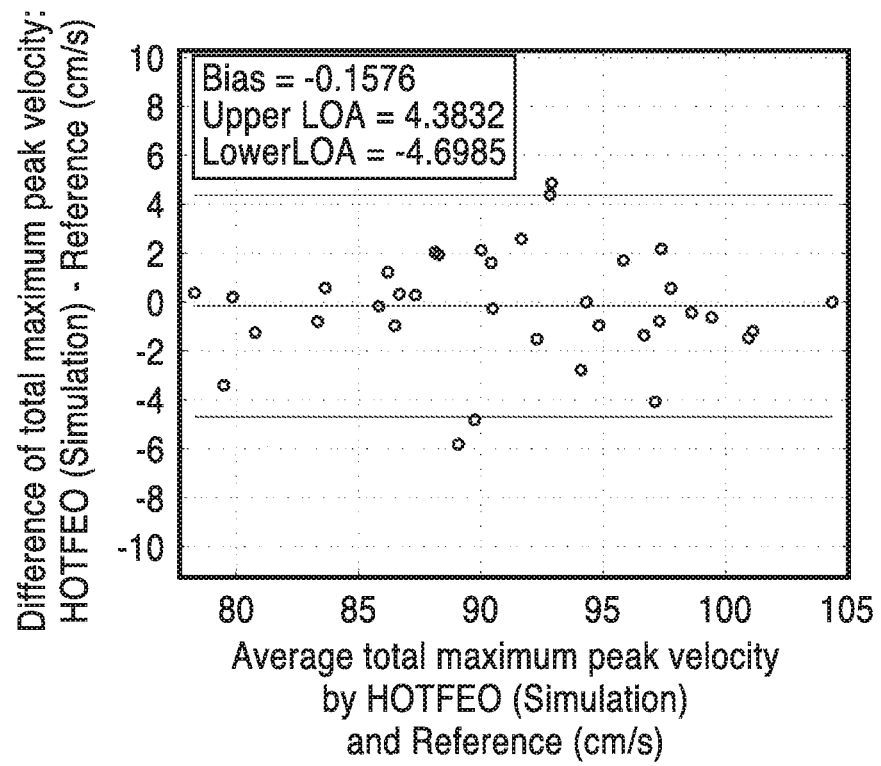

FIG. 10B shows Bland-Altman plots of total maximum peak velocity measurement between simulated HOTFEO and reference FC/3FE.

Figure 11A:
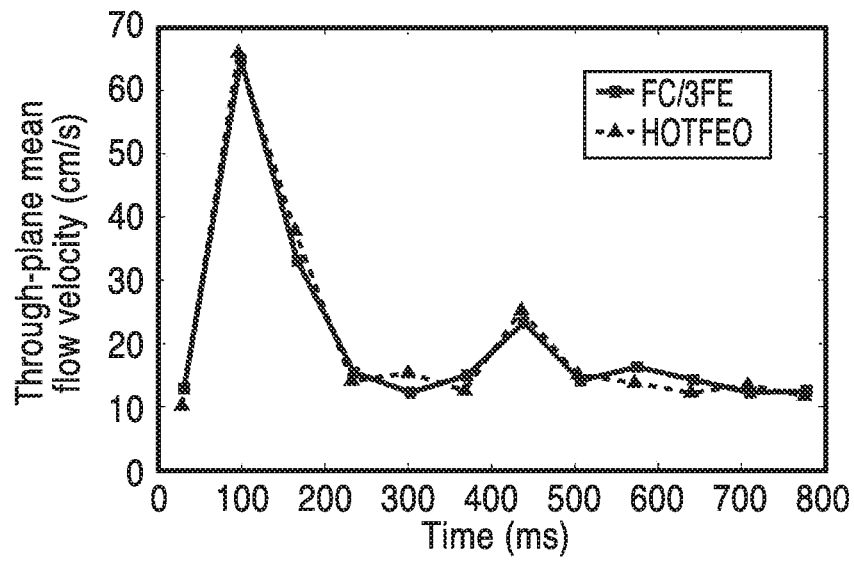

FIG. 11A shows a plot of the total mean flow velocity waveforms of 4D reference FC/3FE PC-MRI and 4D HOTFEO.

Figure 11B:
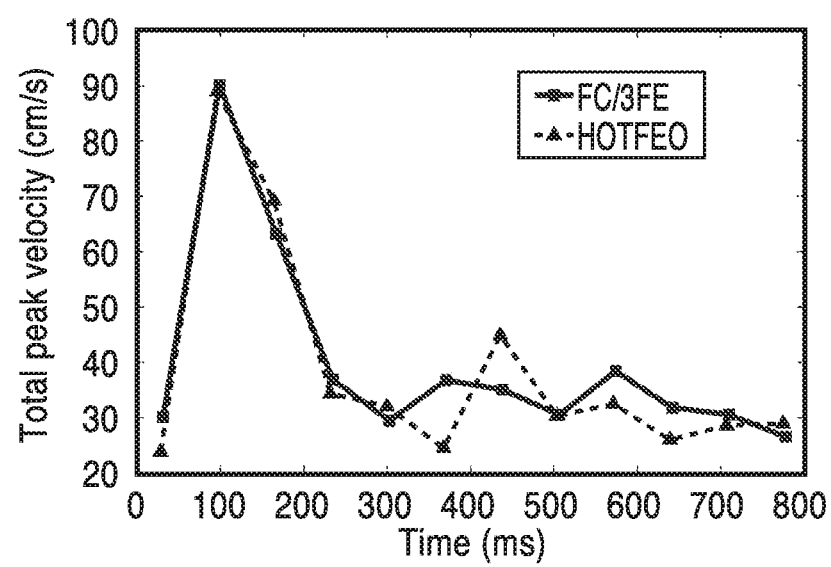

FIG. 11B shows a plot of the total peak velocity waveforms of 4D reference FC/3FE PC-MRI and 4D HOTFEO.

Figure 12A:
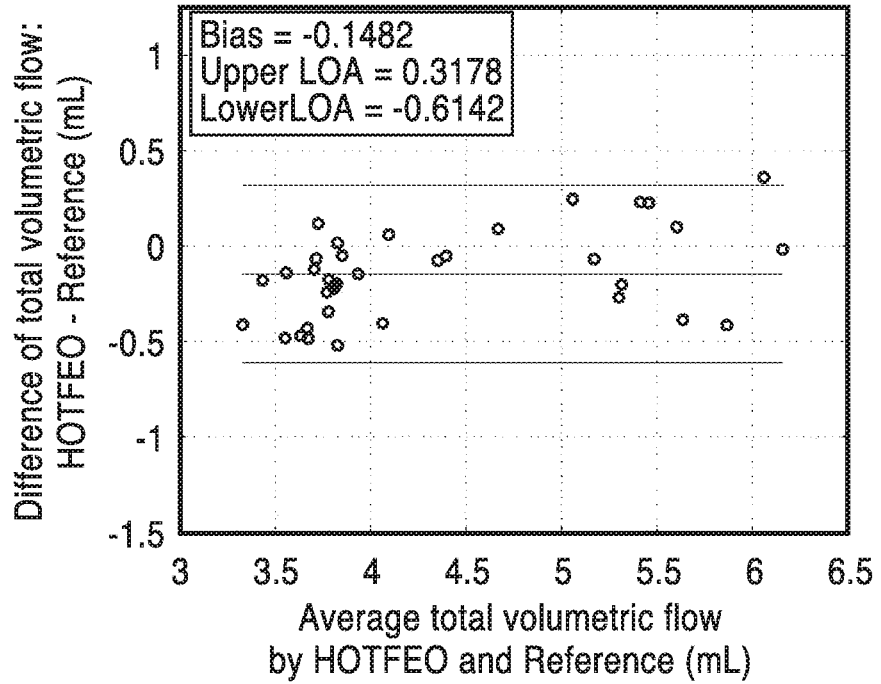

FIG. 12A shows Bland-Altman plots of total volumetric flow measurement between 4D reference FC/3FE and 4D HOTFEO.

Figure 12B:
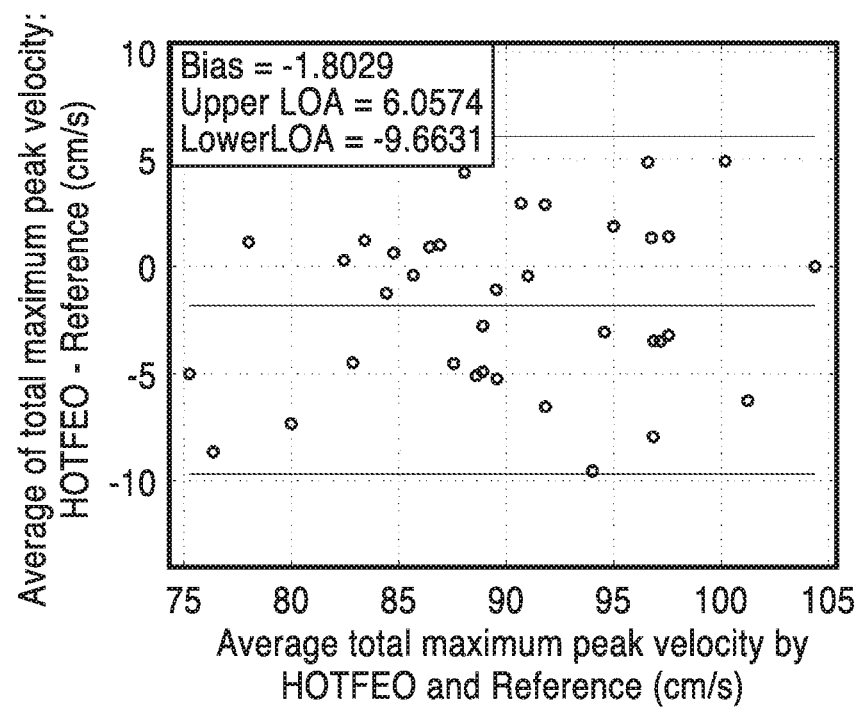

FIG. 12B shows Bland-Altman plots of total maximum peak velocity measurement between 4D reference FC/3FE and 4D HOTFEO.

DETAILED DESCRIPTION

In common carotid arteries (CCAs), the blood flow tends to be laminar flow, and the velocity direction (as opposed to magnitude) does not change significantly within a short period time (e.g. duration of two cardiac phases). associating with the property that phase signal of FC images does not change significantly, Eq. 1 provides the following velocity direction constraint for cardiac phase n and n+1:

$$\Phi_{FC,n} = \underset{\Phi_{FC,n}}{\operatorname{argmin}} \left| |\vec{V_n} \cdot \vec{V_{n+1}}| - |\vec{V_n}| * |\vec{V_{n+1}}| \right|. \qquad \text{Eq. 1}$$

In Eq. 1, $\phi_{FC,n} = \phi_{FC,n+1}$ represents FC phase signal (i.e. FC background phase), and the two velocity vectors of the two cardiac phases are:

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}) \text{ and}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n}).$$

The terms $\Phi_{FEx,n}$, $\Phi_{FEy,n}$ and $\Phi_{FEz,n}$ are the acquired FE phase signals for cardiac phase n in the x, y and z directions, respectively, and $\Phi_{FEx,n+1}$, $\Phi_{FEy,n+1}$ and $\Phi_{FEz,n+1}$ are the acquired FE phase signals for cardiac phase n+1 in the x, y and z directions, respectively. $\vec{V_n}$ and $|\vec{V_{n+1}}|$ are the velocity magnitudes for cardiac phases n and n+1, respectively. $\vec{V_n} \cdot \vec{V_{n+1}}$ is the dot product of two velocity vectors that contains 3D velocity information. Eq. 1 essentially calculates the background phase $\Phi_{FC,n}$ that yields the smallest angle between the blood flow velocity vectors between two successive cardiac phases. It is assumed that the smallest angle corresponds to the smallest difference between the dot product of the two velocity vectors and the product of the length of the two vectors, as shown in Eq. 1.

Figure 4:
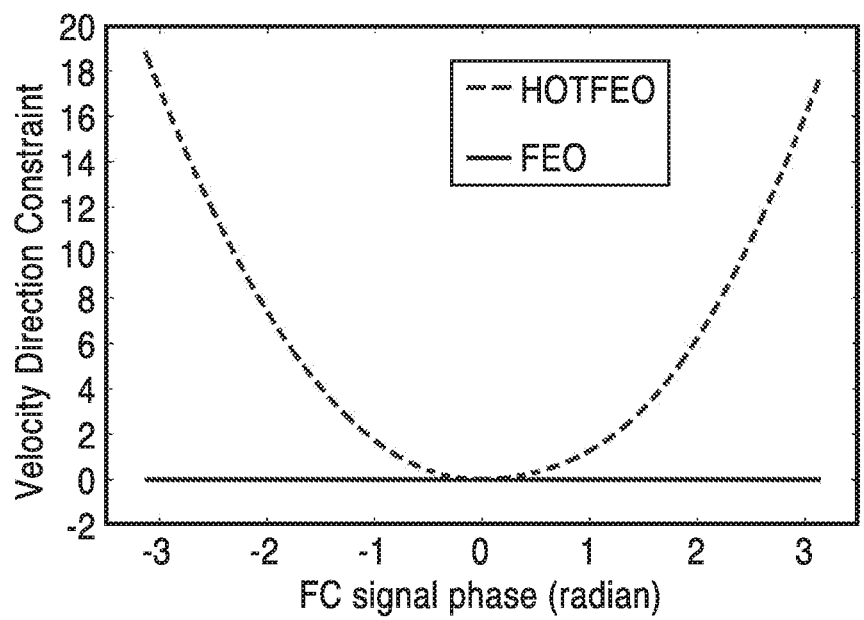
FIG. 4 is a plot comparing the velocity constraint as function of FC signal phase with two consecutive velocities having equal magnitude and direction.

While the constraint of velocity direction has the potential to calculate the background phase signal without acquiring the FC data, the velocity direction constraint itself may have two ill-conditions: 1) the two consecutive velocities equal to each other ($\vec{V_n} = |\vec{V_{n+1}}|$, which are likely to happen in diastolic cardiac phases; and 2) where the three-directional projected velocities equal to each other ($V_{x,n} = V_{y,n} = V_{z,n}$, or $\Phi_{FEx,n} = \Phi_{FEy,n} = \Phi_{FEz,n}$), which may happen in certain orientations of blood vessels to the three encoding directions in 4D flow acquisitions. As shown in FIG. 4 (solid curve), the constraint constantly equals to 0 under the above two circumstances. These ill-conditions might limit the applications of the velocity direction constraint, such as for diastolic velocity calculations or imaging in target anatomy with various velocity distributions, e.g. blood vessels such as aortic arch and circle of willis.

Figure 1:
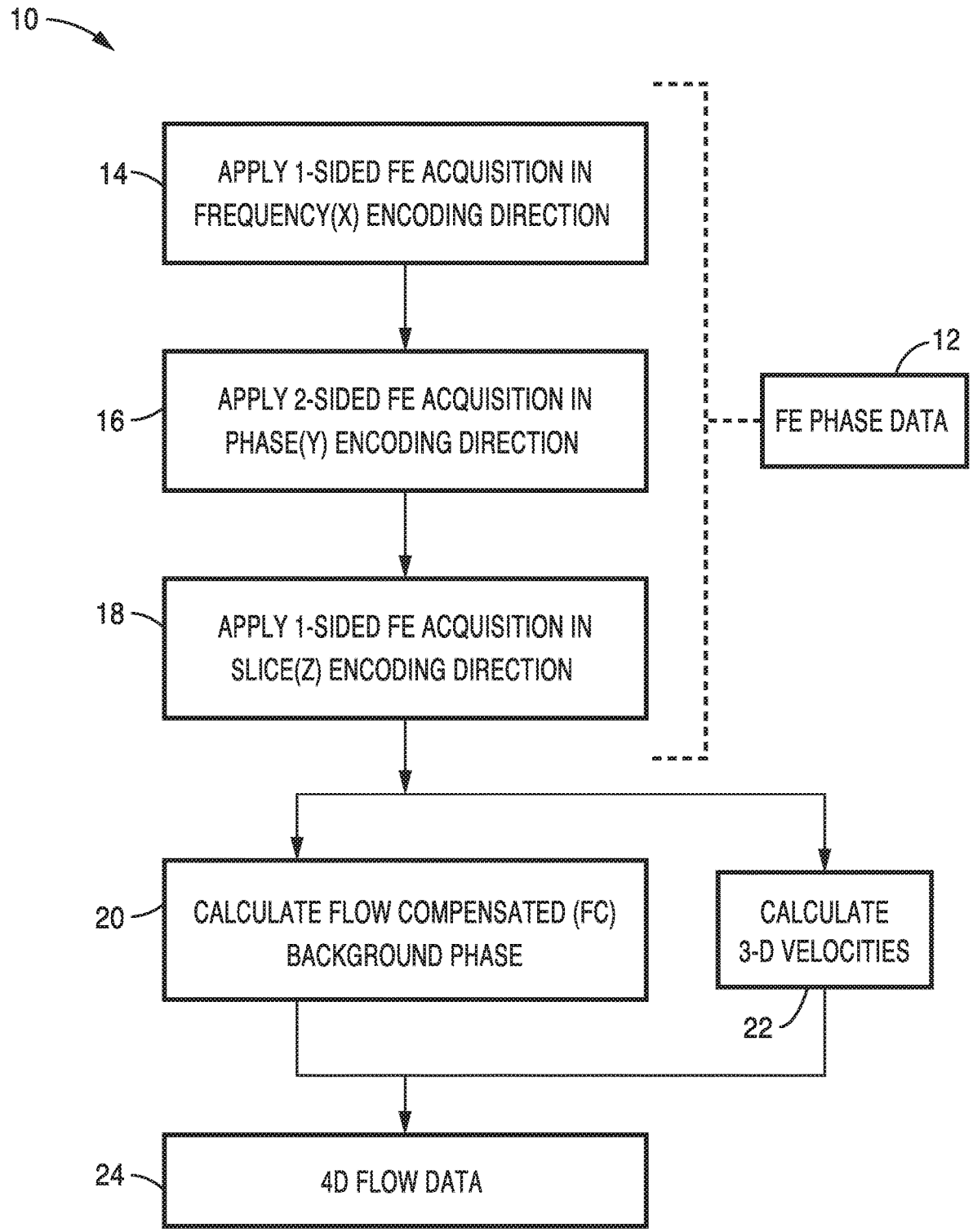
FIG. 1 is schematic flow diagram of the HOTFEO acquisition scheme for calculating 4D flow characteristics in accordance with the present description.
Figure 2:
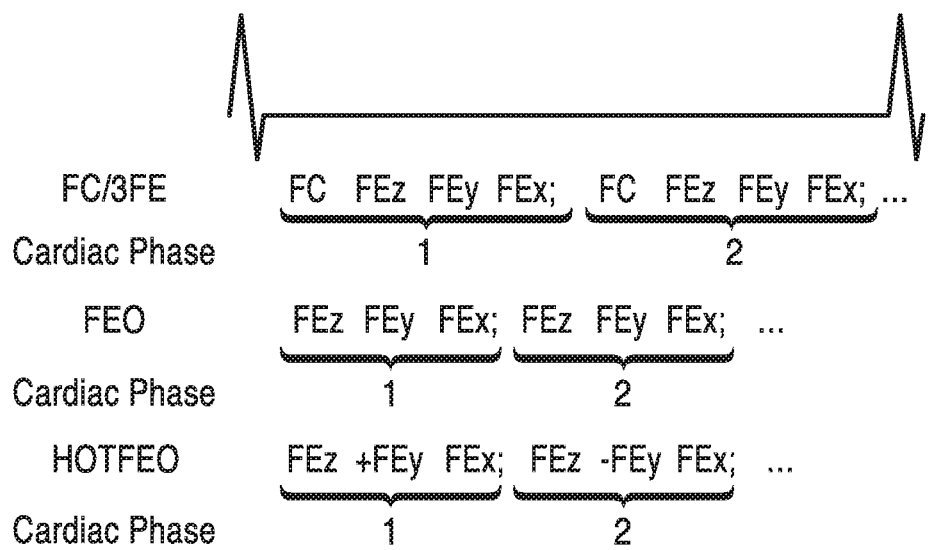
FIG. 2 is a schematic phase diagram comparing the HOTFEO acquisition scheme with FEO and FC/3FE.

To address the above ill-conditions of the constraint and improve calculation accuracy of FC phase signal, the HOTFEO acquisition method 10 of FIG. 1 is employed. The HOTFEO acquisition method in comparison to FEO and FC/3FE schemes is also shown in the phase diagram of FIG. 2. As shown in FIG. 2, HOTFEO applies interleaved two-sided FE acquisitions in one direction (e.g. the y-(phase-encoding) direction), and conventional one-sided FE acquisitions in the remaining directions (e.g. x/z-directions, i.e. frequency/slice-encoding directions). FEO applies strictly one-sided FE acquisitions only in all directions, while FC/3FE applies one-sided FE acquisitions in all directions along with acquisition of flow-compensated (FC) data.

Referring back to the flow diagram of FIG. 1, the HOTFEO acquisition method 10, one-sided flow-encoded MRI acquisition is applied at step 14 in the frequency-encoding (x) direction and at step 18 in the slice-encoding (z) direction, while two-sided flow-encoded MRI acquisition is applied at step 16 in the phase-encoding (y) direction. As seen in FIG. 2, interleaved, two-sided FE is applied in the y-direction by alternating the polarity of the FE gradient between successive cardiac phases While two-sided FE acquisition is shown specifically in the y-direction in FIG. 1 and FIG. 2, it is appreciated that two-sided FE acquisition can be applied on any one or two direction(s) of the three (x, y, z) directions. The two-sided FE was chosen for the phase-encoding direction (y-direction), because it did not increase TE/TR of the pulse sequence, as will be explained in further detail below. Furthermore, it is appreciated that the order of acquisition between x, y, and z directions may also be alternated as appropriate.

Referring back to FIG. 1, various physiological characteristics of the target anatomy may be measured from the acquired FE phase data 12, such as blood flow and blood velocity. In a preferred embodiment, the acquired FE phase data 12 is used to calculate the flow-compensated (FC) background phase at step 20 using Eq. 1. Additionally, three-directional velocities of each cardiac phase may be calculated at step 22 by subtracting the background phase from the FE signal phases 12. By subtracting the phase images of the each flow sensitive scan from the phase of the referenced flow compensated scan, the 4D flow data 24 are obtained. The HOTFEO acquisition method 10 can be applied at systole and diastole, for non-straight blood vessels.

Further processing steps may include correcting for eddy current, Maxwell terms and gradient field nonlinearities, in addition to fast MRI techniques such as non-Cartesian sampling, parallel imaging, and compressed sensing to further refine the data and/or achieve even higher acceleration rates. In one embodiment, eddy current correction is applied by subtracting the phase images of a steady phantom repeating scans with the same parameters from the in vivo scans. View-sharing techniques may also be employed to help improved the temporal resolution.

Figure 3:
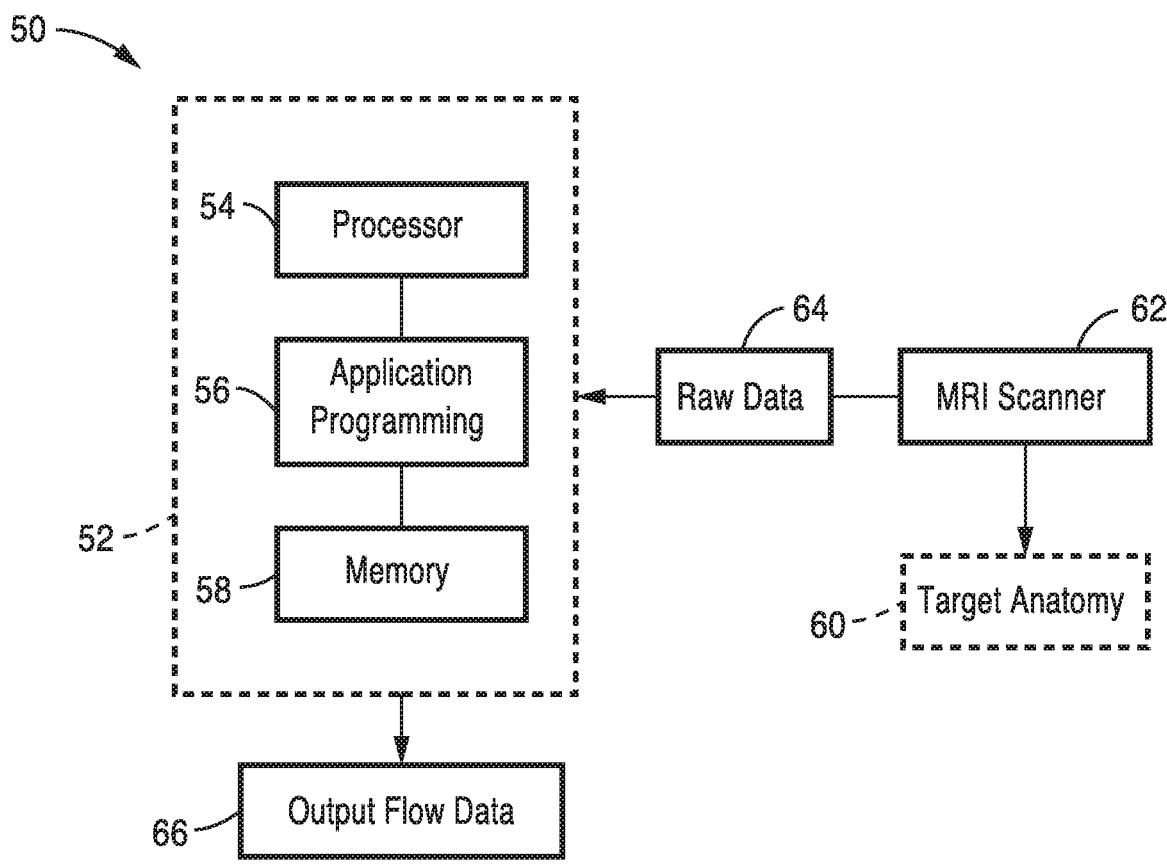
FIG. 3 is a schematic diagram for a system incorporating HOTFEO acquisition for calculating 4D flow characteristics in accordance with the present description.

FIG. 3 shows a schematic diagram for a system 50 incorporating HOTFEO acquisition for calculating 4D flow characteristics in accordance with the present description. System 50 includes a computer or server 52 comprising a processor 54, and application programming 56 stored in memory 58, the application programming 56 comprising instructions for receiving raw data of the target anatomy 60 from MRI scanner 62, and applying HOTFEO acquisition method 10 to output flow data (e.g. any of background FC phase 20, 3-D velocities 22, or 4D flow data 24 shown in FIG. 1). Application programming 56 may further include instructions for performing post-processing techniques such as eddy current correction, fast MRI, and view-sharing.

Additional supporting calculations are as follows:

Assuming that the FC phase signal does not change between cardiac phases n and n+1, i.e. $\phi_{0,n}=\phi_{0,n+1}$, the two velocity vectors of the two cardiac phases are:

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}) \text{ and}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n}).$$

Expanding the velocity direction constraint (Eq. 1) yields:

$$\left\| \vec{V_n} \cdot \vec{V_{n+1}} \right| - |\vec{V_n}| * |\vec{V_{n+1}}| \right\| = \left\| V_{x,n} * V_{x,n+1} + V_{y,n} * V_{y,n+1} + V_{z,n} * V_{z,n+1} \right| -$$
$$\sqrt{V_{x,n}^2 + V_{y,n}^2 + V_{z,n}^2} * \sqrt{V_{x,n+1}^2 + V_{y,n+1}^2 + V_{z,n+1}^2} \Bigg| =$$
$$\frac{VENC}{\pi} \Big\| (\Phi_{FEx,n} - \Phi_{FC,n}) * (\Phi_{FEx,n+1} - \Phi_{FC,n}) + (\Phi_{FEy,n} - \Phi_{FC,n}) * (\Phi_{FEy,n+1} - \Phi_{FC,n}) +$$
$$(\Phi_{FEz,n} - \Phi_{FC,n}) * (\Phi_{FEz,n+1} - \Phi_{FC,n}) | -$$
$$\sqrt{(\Phi_{FEx,n} - \Phi_{FC,n})^2 + (\Phi_{FEy,n} - \Phi_{FC,n})^2 + (\Phi_{FEz,n} - \Phi_{FC,n})^2} *$$
$$\sqrt{(\Phi_{FEx,n+1} - \Phi_{FC,n})^2 + (\Phi_{FEy,n+1} - \Phi_{FC,n})^2 + (\Phi_{FEz,n+1} - \Phi_{FC,n})^2} \Big|.$$

Eq. 2

For the first of the two ill-conditions, when $\vec{V_n} = |\vec{V_{n+1}}|$, i.e. $\Phi_{FEx,n}=\Phi_{FEx,n+1}$, $\Phi_{FEy,n}=\Phi_{FEy,n+1}$ and $\Phi_{FEz,n}=\Phi_{FEz,n+1}$, Eq. 2 becomes:

$$\frac{VENC}{\pi} \Big\| (\Phi_{FEx,n} - \Phi_{FC,n}) * (\Phi_{FEx,n} - \Phi_{FC,n}) +$$
$$(\Phi_{FEy,n} - \Phi_{FC,n}) * (\Phi_{FEy,n} - \Phi_{FC,n}) + (\Phi_{FEz,n} - \Phi_{FC,n}) * (\Phi_{FEz,n} - \Phi_{FC,n}) | -$$
$$\sqrt{(\Phi_{FEx,n} - \Phi_{FC,n})^2 + (\Phi_{FEy,n} - \Phi_{FC,n})^2 + (\Phi_{FEz,n} - \Phi_{FC,n})^2} *$$
$$\sqrt{(\Phi_{FEx,n} - \Phi_{FC,n})^2 + (\Phi_{FEy,n} - \Phi_{FC,n})^2 + (\Phi_{FEz,n} - \Phi_{FC,n})^2} \Big| =$$
$$\frac{VENC}{\pi} \Big\| (\Phi_{FEx,n} - \Phi_{FC,n})^2 + (\Phi_{FEy,n} - \Phi_{FC,n})^2 + (\Phi_{FEz,n} - \Phi_{FC,n})^2 | -$$
$$| (\Phi_{FEx,n} - \Phi_{FC,n})^2 + (\Phi_{FEy,n} - \Phi_{FC,n})^2 + (\Phi_{FEz,n} - \Phi_{FC,n})^2 \Big\| = 0.$$

Eq. 3

For the second condition that the magnitude of three-directional velocities equals to each other ($V_{x,n}=V_{y,n}=V_{z,n}$ or $\Phi_{FEx,n}=\Phi_{FEy,n}=\Phi_{FEz,n}$), Eq. 1 becomes:

$$\frac{VENC}{\pi}\|(\Phi_{FEx,n}-\Phi_{FC,n})*(\Phi_{FEx,n+1}-\Phi_{FC,n})+$$
$$(\Phi_{FEx,n}-\Phi_{FC,n})*(\Phi_{FEx,n+1}-\Phi_{FC,n})+(\Phi_{FEx,n}-\Phi_{FC,n})*(\Phi_{FEx,n+1}-\Phi_{FC,n})|-$$
$$\sqrt{(\Phi_{FEx,n}-\Phi_{FC,n})^2+(\Phi_{FEx,n}-\Phi_{FC,n})^2+(\Phi_{FEx,n}-\Phi_{FC,n})^2} *$$
$$\sqrt{(\Phi_{FEx,n+1}-\Phi_{FC,n})^2+(\Phi_{FEx,n+1}-\Phi_{FC,n})^2+(\Phi_{FEx,n+1}-\Phi_{FC,n})^2}\Big| =$$
$$\frac{VENC}{\pi}\|3*(\Phi_{FEx,n}-\Phi_{FC,n})*(\Phi_{FEx,n+1}-\Phi_{FC,n})|-$$
$$\sqrt{3*(\Phi_{FEx,n}-\Phi_{FC,n})^2}*\sqrt{3*(\Phi_{FEx,n+1}-\Phi_{FC,n})^2}\Big| =$$
$$\frac{VENC}{\pi}\|3*(\Phi_{FEx,n}-\Phi_{FC,n})*(\Phi_{FEx,n+1}-\Phi_{FC,n})|-$$
$$|3*(\Phi_{FEx,n}-\Phi_{FC,n})*(\Phi_{FEx,n+1}-\Phi_{FC,n})|\| = 0.$$

Eq. 4

In the two ill-conditions, the velocity direction constraint is underdetermined without a unique solution. By applying the HOTFEO acquisition scheme of the present description, $V_{y,n}$ and $V_{y,n+1}$ have opposite sign of velocity magnitudes in y-direction. In order to maintain the true physics meaning of velocity direction constraint, Eq. 1 is modified as:

$$\left\|\left|\vec{V_n}\cdot\vec{V_{n+1}}\right|-|\vec{V_n}|*|\vec{V_{n+1}}|\right\| =$$
$$\Big||V_{x,n}*V_{x,n+1}+V_{y,n}*V_{y,n+1}+V_{z,n}*V_{z,n+1}|-\sqrt{V_{x,n}^2+V_{y,n}^2+V_{z,n}^2}*\sqrt{V_{x,n+1}^2+V_{y,n+1}^2+V_{z,n+1}^2}\Big| =$$
$$\frac{VENC}{\pi}\|(\Phi_{FEx,n}-\Phi_{FC,n})*(\Phi_{FEx,n+1}-\Phi_{FC,n})-(\Phi_{FEy,n}-\Phi_{FC,n})*(\Phi_{FEy,n+1}-\Phi_{FC,n})+(\Phi_{FEz,n}-\Phi_{FC,n})*$$
$$(\Phi_{FEz,n+1}-\Phi_{FC,n})\Big|-\sqrt{(\Phi_{FEx,n}-\Phi_{FC,n})^2+(\Phi_{FEy,n}-\Phi_{FC,n})^2+(\Phi_{FEz,n}-\Phi_{FC,n})^2}*$$
$$\sqrt{(\Phi_{FEx,n+1}-\Phi_{FC,n})^2+(\Phi_{FEy,n+1}-\Phi_{FC,n})^2+(\Phi_{FEz,n+1}-\Phi_{FC,n})^2}\Big|.$$

Eq. 5

A minus sign is used before the $V_{y,n}*V_{y,n+1}$ term because $V_{y,n}$ and $V_{y,n+1}$ have opposite flow velocity encoding. Meanwhile, mathematically the constraint has been constructed as a parabola-like function. For the first ill-condition, which in HOTFEO technique, we have $\Phi_{FEx,n}=\Phi_{FEx,n+1}$, $\Phi_{FEy,n}\neq\Phi_{FEx,n+1}$ and $\Phi_{FEz,n}=\Phi_{FEz,n+1}$, thus Eq. 3 becomes:

$$\frac{VENC}{\pi}\|(\Phi_{FEx,n}-\Phi_{FC,n})*(\Phi_{FEx,n}-\Phi_{FC,n})-$$
$$(\Phi_{FEy,n}-\Phi_{FC,n})*(\Phi_{FEy,n+1}-\Phi_{FC,n})+(\Phi_{FEz,n}-\Phi_{FC,n})*(\Phi_{FEz,n}-\Phi_{FC,n})|-$$
$$\sqrt{(\Phi_{FEx,n}-\Phi_{FC,n})^2+(\Phi_{FEy,n}-\Phi_{FC,n})^2+(\Phi_{FEz,n}-\Phi_{FC,n})^2} *$$
$$\sqrt{(\Phi_{FEx,n}-\Phi_{FC,n})^2+(\Phi_{FEy,n+1}-\Phi_{FC,n})^2+(\Phi_{FEz,n}-\Phi_{FC,n})^2}\Big|.$$

Eq. 6

Qualitatively, the dot product part has second order term, $\Phi_{FC,n}^2$, and second order term of the times between two velocity magnitudes closely, not strictly, equal to $3*\Phi_{FC,n}^2$. When they subtract each other, the constraint will become a parabola function with second order term $2*\Phi_{FC,n}^2$, which may have a unique solution $\Phi_{FC,n}$. A series of numerical simulations were performed by assigning various $\Phi_{FEx/y/z,n}$ to summarize the function behavior and draw a conclusion. Based on numerical simulations of the constraint as a function of $\Phi_{FC,n}$, the minimal point of the function (=0) is when $\Phi_{FC,n}$ satisfies $\Phi_{FEy,n}-\Phi_{FC,n}=-(\Phi_{FEy,n+1}-\Phi_{FC,n})$, i.e. the theoretical solution matches the initial hypothesis: $\vec{v_n}=|\vec{v_{n+1}}|$.

As for the second ill-condition, tt has two minimal points, one is the solution (=0 in the example) and its value falls in the range $(\Phi_{FEy,n+1},\Phi_{FEy,n})$ (assuming $\Phi_{FEy,n}>\Phi_{FEy,n+1}$). The other is when $\Phi_{FC,n}$ may equal to either $\Phi_{FEy,n}$ or $\Phi_{FEy,n+1}$, and this extraneous root can be excluded by limiting the solution range within $(\Phi_{FEy,n+1},\Phi_{FEy,n})$.

According to the above calculations, the constraint mathematically becomes a parabola-like function (as shown in the dashed curve of FIG. 4) without changing the original physics meaning of dot product between two velocity vectors. Thus, it can ensure a unique solution of $\Phi_{FC,n}$ within the searching range $(\Phi_{FEy,n},\Phi_{FEy,n+1})$, and an accurate estimation of FC signal phase, whereat the constraint of FEO (solid line in FIG. 4) is ill-conditioned and not able to determine the FC signal phase.

Qualitatively, HOTFEO acquisition changes the mathematical function of the constraint to a $\sim 2*\Phi_{FC,n}^2$ behavior parabolic function, thus ensuring a unique solution of FC signal phase. Combined with a solution searching range $(\Phi_{FEy,n+1},\Phi_{FEy,n})$ (assuming $\Phi_{FEy,n}>\Phi_{FEy,n+1}$), this may aid in excluding extraneous root generated from the second ill-condition. More importantly, the HOTFEO acquisition scheme also improves the calculation accuracy of $\Phi_{FC,n}$. The function of constraint without hybrid FE was flatter than HOTFEO. Consequently, the minimal point of the constraint might be significantly influenced by noise factors, as shown in the numerical simulation.

Example 1

The HOTFEO acquisition scheme was evaluated in healthy volunteers and compared with conventional FC/3FE acquisitions in 2D and 4D flow quantifications. To validate the HOTFEO acquisition scheme, flow measurements based on 2D/4D HOTFEO acquisitions with three FE directions were compared with conventional 2D/4D FC/3FE PC-MRI. All studies were performed on a 3 T scanner with 4-channel neck coils (Skyra, Siemens, Germany).

Numerical simulations were first performed to study the impact of signal-to-noise ratio (SNR) and velocity magnitude ratio (VR=$|\overline{V_{n+1}}/\overline{V_n}|$) on the accuracy of FC calculation between the HOTFEO acquisition scheme and FEO technique (i.e. all one-sided FE acquisitions in three directions). We assumed $\overline{V}_n$=(−0.2, 1.5, 2.4) and $\Phi_{FC,n}$=0 as initial conditions, associated with SNR=20, 30, 40, 50 and VR=0.1, 0.25, 0.5, 0.75, 0.9 to compare the FC calculation accuracy of the two techniques. For each combination of SNR and VR, we repeated 100 times with Gaussian noise distribution satisfied the SNR. Root of Mean Square Error (RMSE) was used to indicate the FC calculation accuracy.

Six volunteers were recruited in retrospective in vivo study. They were scanned by a standard 4D flow sequence at the CCAs. The sequence was implemented with: Velocity ENCoding (VENC)=100-105 cm/s, flip angle=20°, readout bandwidth=815 Hz/Pixel, TE=3.35 ms, Views-per-segment=3, temporal resolution=67.92 ms, acquired matrix=256×176×10, FOV=256×176×18.2 mm$^3$, and spatial resolution=1×1×1.82 mm$^3$. All scans were acquired during free breathing with prospective ECG gating. Reference 4D flow data were simulated to the HOTFEO acquisition scheme as shown in FIG. 1 and FIG. 2. Eq. 1 was used to calculate FC signal phase followed by three-directional velocities. The simulated results from HOTFEO reconstruction, including total volumetric flow and total peak velocity ($=\sqrt{V_x^2+V_y^2+V_z^2}$), were compared with reference data as ground truth.

After the retrospective study, six additional volunteers were scanned at the CCAs using: 1) the standard 2D FC/3FE PC-MRI sequence, 2) the prospective 2D HOTFEO sequence, 3) the standard 4D flow sequence, 4) the prospective 4D flow HOTFEO sequence. The four sequences were implemented with: VENC=100-105 cm/s, flip angle=20°. The parameters used by both 2D sequences were: readout bandwidth=500 Hz/Pixel, TE=3.72 ms, Views-per-segment=3 (FC/3FE) and 4 (HOTFEO), temporal resolution=72.48 ms, acquired matrix=256×176, FOV=256×176 mm$^2$, slice thickness=7 mm. The parameters used by both 4D flow sequences were: readout bandwidth=815 Hz/Pixel, TE=3.35 ms, Views-per-segment=3 (FC/3FE) and 4 (HOTFEO), temporal resolution=67.92 ms, acquired matrix=256×176×10, FOV=256×176×18.2 mm$^3$. All scans were acquired during free breathing with prospective ECG gating. Eddy current correction was applied in the in vivo studies data sets by subtracting the phase images of a steady phantom repeating scans with the same parameters from the in vivo scans. HOTFEO achieved 4/3-fold acceleration by using 4 views-per-segment compared with 3 views-per-segment FC/3FE data sets. By subtracting the phase images of the each flow sensitive scan from the phase of the referenced flow compensated scan, the 4D flow data were obtained.

Region of interest (ROI) contours of the entire CCA lumen were drawn based on magnitude DICOM images of each cardiac phase. For the all in vivo studies, Bland-Altman plots were used to compare the agreements of total volumetric flows and maximum total peak velocities between reference FC/3FE and HOTFEO techniques. In retrospective in vivo study, RMSE and two-sided paired t-test (P<0.05 indicating statistical significance) were used to compare the through-plane mean flow velocities and the total velocities ($=\sqrt{V_x^2+V_y^2+V_z^2}$) calculated from the FC/3FE reference and the HOTFEO.

Compared with the FC and three-directional FE acquisitions (FC/3FE), Bland-Altman tests showed that 4/3-fold accelerated HOTFEO acquisition resulted in relatively small bias error for total volumetric flow (0.89% for prospective 2D, −1.19% for retrospective 4D data, and −3.40% for prospective 4D data), and total maximum peak velocity (0.50% for prospective 2D, −0.17% for retrospective 4D data, and −2.00% for prospective 4D data) measurements in common carotid arteries.

Figure 5:
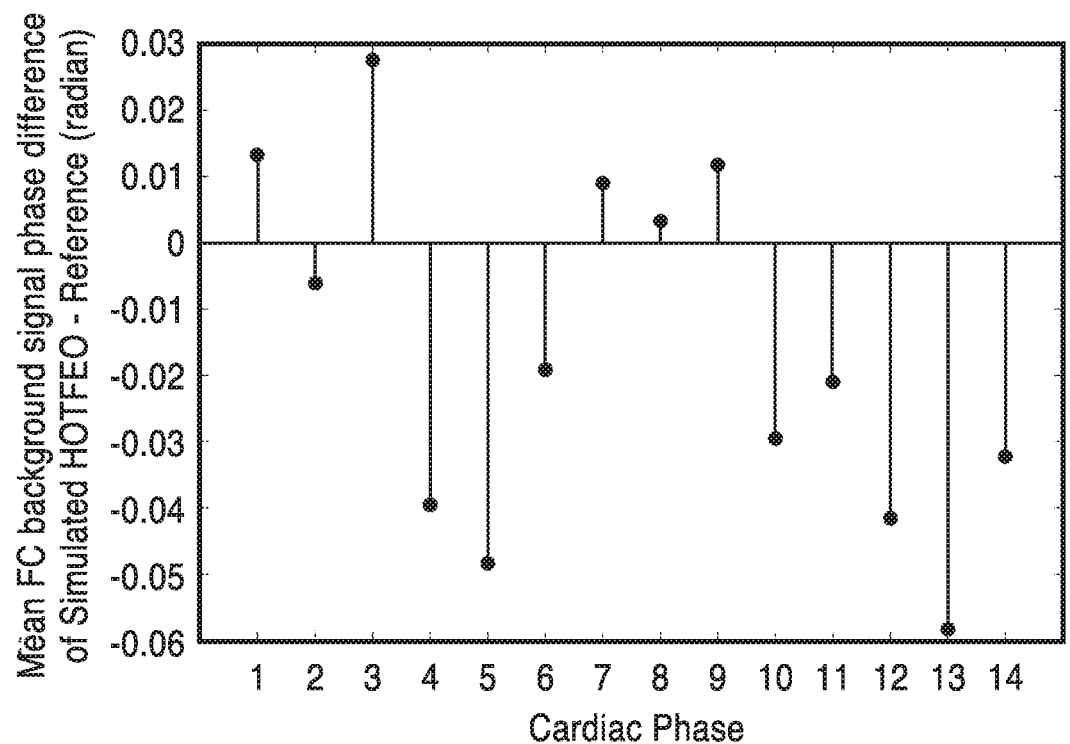
FIG. 5 is a plot illustrating the difference between the acquired FC background phase and the background phase from a healthy volunteer.

FIG. 5 shows the difference between the acquired FC background phase and the background phase from a healthy volunteer calculated using Eq. 1. Compared with standard 4D flow, simulated HOTFEO showed that the FC calculation is accurate with mean RMSE=0.04 (range: 0.02-0.06) rad.

Table 1 shows the RMSE of calculated FC under various SNR and VR combinations. Both HOTFEO and FEO tend to have more accurate estimation of FC signal (smaller RMSE) with higher SNR (as shown in FIG. 6B). As shown in FIG. 6A, when velocity magnitudes become close (i.e. 1−VR becomes smaller), the RMSE of FC calculation by FEO has an inverse correlation with $$\left(1-\frac{|V_{n+1}|}{|V_n|}\right),$$

while the HOTFEO acquisition method maintains the nearly the same accuracy, but with very slight increase and the RMSEs of the HOTFEO acquisition method are always smaller than that of FEO. The HOTFEO acquisition method has more accurate and consistent FC estimations than FEO. From FIG. 6A, it is expected that when $|V|=|V_{n+1}|$, i.e. 1−VR=0, the RMSE of FC calculation by FEO technique will become infinite large, but the HOTFEO acquisition method can still provide accurate FC estimation.

An example of through-plane mean flow velocity waveform and total peak velocity waveform from one slice of one volunteer's data set is shown in FIG. 7A and FIG. 7B, respectively. The HOTFEO acquisition method and reference FC/3FE method showed good agreement on both waveforms. Three slices (slice 3,5,8) of both CCAs of six volunteers data sets were selected to compare the measurements of the mean flow velocity and total peak velocity waveforms. 36 total measurements of velocity waveforms showed that the average RMSEs of mean flow velocity was 1.22 (range 0.65-2.07) cm/s and total peak velocity was 3.23 (range 1.68-5.09) cm/s, which showed good agreements between two techniques. The potential errors might come from the noise that reversed along velocities in y-direction during simulation.

The Bland-Altman plot of total volumetric flow measurement is shown in FIG. 8A, the bias is 0.0554 mL (−1.19% relative bias error) and the 95% confidence interval (CI) was

[−0.2399, 0.1292] mL. The Bland-Altman plot of total maximum peak velocity measurement is shown in FIG. 8B, the bias is −0.1576 cm/s (−0.17% relative bias error) and the 95% CI was [−4.6985, 4.3832] cm/s. The Bland-Altman plot indicated a good agreement between the HOTFEO acquisition method and reference FC/3FE on total volumetric flow and maximum peak velocity measurements.

FIG. 9A and FIG. 9B show examples of 2D through-plane mean velocity and total peak velocity waveforms comparisons, respectively, between reference FC/3FE and the HOTFEO acquisition method. FIG. 11A and FIG. 11B show examples of 4D through-plane mean velocity and total peak velocity waveforms comparisons, respectively, between reference FC/3FE and the HOTFEO acquisition method. The two techniques show good agreement and consequently result in good agreements of total volumetric flow and total maximum peak velocity measurements.

Bland-Altman plots of total volumetric flow within the cardiac cycle measured in the left and right CCAs of the six volunteers using HOTFEO and FC/3FE PC-MRI are shown in FIG. 10A and FIG. 12A. For 2D PC-MRI study, the bias was 0.0388 mL (0.89% relative bias error) with the 95% CI [−0.1514, 0.2291] mL. For 4D PC-MRI study (slice 3,5,8 were chosen for relative measurements, same as the total maximum peak velocity measurements), the bias was −0.1482 mL (−3.40% relative bias error) with the 95% CI [−0.6142, 0.3178] mL. The Bland-Altman plots of maximum total peak velocity (FIG. 10B and FIG. 12B) showed that the bias of 2D study was 0.3729 cm/s (0.50% relative bias error) with the 95% CI [−5.9369, 6.6827] cm/s, and the bias of 4D PC-MRI study was −1.8029 cm/s (2.00% relative bias error) with 95% CI [−9.6631, 6.0574] cm/s. The 2D prospective study showed similar statistics results (bias and 95% CI of total volumetric flow and maximum total peak velocity) when compared to retrospective 4D flow study mainly because the minimal physiological change of volunteers within two 2D scans (<2 minutes). But 4D prospective studies showed lager bias and 95% CI than retrospective study and 2D prospective study, mainly because the total scan time (15 minutes to 20 minutes for FC/3FE and HOTFEO) was significant longer than 2D studies, physiological changes were observable during the scan, such as 20% heart rate change, motion between reference FC/3FE and HOTFEO scans.

The utility of HOTFEO acquisition systems and methods have been demonstrated in PC-MRI with multiple FE acquisitions (2D and 4D flow quantifications) for accelerating the PC-MRI scans to achieve significant savings in total acquisition time. The HOTFEO acquisition method of FIG. 1 and FIG. 2 is a pure phase image-based reconstruction technique, therefore other fast MRI techniques, such as parallel imaging, compressed sensing or non-Cartesian readout may be combined to achieve even higher acceleration rates. Moreover, it can be used to improve temporal resolution and footprint for PC-MRI. Typically, the temporal resolution and temporal footprint of PC-MRI with three-directional velocity encodings equal to 4*TR*views-per-segment. With certain views-per-segment and optimized TR, the temporal resolution and temporal footprint can no longer be improved by fast MRI techniques.

View-sharing techniques may help improved the temporal resolution but not the temporal footprint, which may still cause the underestimation of maximum peak velocity due to the temporal averaging by long temporal footprint. FC signal phase is the parameter that can be shared without significantly introducing errors to peak velocity measurements, because it reflects the background phase which is not expected to change significantly in a relative short period of time. In the HOTFEO acquisition and method, the FC signal is only shared within two consecutive cardiac phases (about 140 ms), and it does not introduce significant errors into the total maximum peak velocity measurements as view-sharing techniques generally do. Thus, the HOTFEO acquisition method can improve both temporal resolution and temporal footprint to 3*TR*views-per-segment by forgoing the FC acquisition. When changing views-per-segment (=1, 2, 3 . . . ), the temporal resolution has a smoother step of increase (=3TR, 6TR, 9TR . . . ) compared with conventional FC/3FE PC-MRI (=4TR, 8TR, 12TR . . . ). The improved temporal resolution is expected to provide more accurate estimation of total maximum peak velocity.

The HOTFEO acquisition method has limited effect on increasing TE/TR. While two-sided FE acquisition can be applied on any one or two direction(s) of the three directions, the two-sided FE was preferably applied on phase-encoding direction (y-direction), because it did not increase TE/TR of the pulse sequence. The minimal TE/TR was achieved in PC-MRI sequence by partially canceling certain one-sided FE gradient with slice refocusing (z-direction) or dephasing gradient (x-direction). However, when the opposite one-sided FE gradient was applied, it could inevitably increase the gradient duration as well as TE/TR.

From the results of total volumetric flow and total maximum peak velocity measurements from both 2D and 4D FC/3FE, it was validated that the velocity direction was consistent within 140 ms time span (=12*TR) in CCAs. The HOTFEO acquisition method is less sensitive to noise, thus it can be used to accelerate FC/3FE PC-MRI, while maintaining the measurement accuracy of blood flow velocity both in systolic (high VNR) and diastolic (low VNR) cardiac phases with minimal limitations.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart (s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A method for time-resolved, three-dimensional (3D) PC-MRI with three-directional velocity encoding of a sample, the method comprising: (a) generating successive time-resolved 3D datasets by performing the steps comprising: (i) acquiring at least one reference image; (ii) performing a one-sided flow-encoded MRI acquisition in an x direction; (iii) performing a two-sided flow-encoded MRI acquisition; and (iv) performing a one-sided flow-encoded MRI acquisition in an z direction; (b) generating visual representations of a field of interest from the data sets; and (c) displaying the visual representations.

2. The method of any preceding embodiment, further comprising: measuring blood flow; and measuring blood velocity.

3. The method of any preceding embodiment, further comprising correcting for phase offset errors due to eddy currents during acquisition of the data sets.

4. The method of any preceding embodiment, wherein the generation of visual representations of a field of interest from the data sets further comprises correcting for Maxwell terms and gradient field nonlinearities.

5. The method of any preceding embodiment, wherein the generation of visual representations of a field of interest from the data sets further comprises applying at least one image based reconstruction selected from the group of parallel imaging, compressed sensing and non-Cartesian readout.

6. An apparatus for time-resolved PC-MRI of a target anatomy, the system comprising: (a) a computer processor; and (b) a non-transitory computer-readable memory storing instructions executable by the computer processor; (c) wherein said instructions, when executed by the computer processor, perform steps comprising: (i) performing one-sided flow-encoded (FE) MRI acquisition of the target anatomy in a first direction of three orthogonal directions associated with an MRI scanner; (ii) performing interleaved, two-sided FE MRI acquisition of the target anatomy in a second direction of the MRI scanner; and (iii) generating successive time-resolved FE datasets of the target anatomy from the one-sided FE MRI acquisition and interleaved, two-sided FE MRI acquisition.

7. The apparatus of any preceding embodiment: wherein the three orthogonal directions comprise a phase-encoding direction, a frequency-encoding direction and a slice-encoding direction of the scanner; and wherein the interleaved, two-sided FE MRI acquisition is applied in the phase-encoding direction.

8. The apparatus of any preceding embodiment, wherein the one-sided FE MRI acquisition is applied in one or more of the frequency-encoding direction and slice-encoding direction.

9. The apparatus of any preceding embodiment, wherein said instructions when executed by the computer processor further perform steps comprising: performing FE MRI acquisition in a third direction of the MRI scanner; wherein one-sided FE MRI acquisition is applied both the frequency-encoding direction and slice-encoding direction.

10. The apparatus of any preceding embodiment: wherein two-sided FE MRI acquisition of the target anatomy is performed in a y-direction associated with the MRI scanner and one-sided FE MRI acquisition is performed in an x-direction associated with the MRI scanner; and wherein said instructions when executed by the computer processor further perform steps comprising: performing one-sided or two-sided FE MRI acquisition in a z direction.

11. The apparatus of any preceding embodiment, wherein interleaved, two-sided FE MRI acquisition comprises alternating a polarity of a FE gradient between successive cardiac phases.

12. The apparatus of any preceding embodiment, wherein said instructions when executed by the computer processor further perform steps comprising: (iv) calculating a flow-compensated (FC) background phase from the FE datasets.

13. The apparatus of any preceding embodiment, wherein flow compensated background phase is calculated according to the equation:

$$\Phi_{FC,n} = \underset{\Phi_{FC,n}}{\operatorname{argmin}} \left\| \vec{V_n} \cdot \vec{V_{n+1}} \right\| - |\vec{V_n}| * |\vec{V_{n+1}}| \right\|; \text{wherein}$$

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}); \text{wherein}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n});$$

and wherein $\phi_{FEx,n}$ are acquired FE phase signals for cardiac phase n in x, y and z directions, respectively, $\phi_{FEx,n+1}$, $\phi_{FEy,n+1}$ and $\phi_{FEz,n+1}$ are the acquired FE phase signals for cardiac phase n+1 in the x, y and z directions, respectively, and $\vec{V_n}$ and $|\vec{V_{n+1}}|$ are the velocity magnitudes for cardiac phases n and n+1, respectively.

14. The apparatus of any preceding embodiment, wherein said instructions when executed by the computer processor further perform steps comprising: measuring one or more physiological characteristics of the target anatomy from the FE datasets.

15. The apparatus of any preceding embodiment: wherein the one or more physiological characteristics of the target anatomy comprises calculating 3-D blood velocities of the target anatomy; wherein the 3-D blood velocities are calculated by subtracting the FC background phase from the time-resolved FE datasets.

16. The apparatus of any preceding embodiment, wherein said instructions when executed by the computer processor further perform steps comprising: generating 4D flow data as a function of the calculated FC background phase and the time-resolved FE datasets.

17. A method for time-resolved, three-dimensional PC-MRI of a target anatomy, the method comprising: performing one-sided flow-encoded (FE) MRI acquisition of the target anatomy in a first direction of three orthogonal directions associated with an MRI scanner; performing interleaved, two-sided FE MRI acquisition of the target anatomy in a second direction of the MRI scanner; and outputting successive time-resolved FE datasets of the target anatomy from the one-sided FE MRI acquisition and interleaved, two-sided FE MRI acquisition.

18. The method of any preceding embodiment: wherein the three orthogonal directions comprise a phase-encoding direction, a frequency-encoding direction and a slice-encoding direction of the scanner; and wherein the interleaved, two-sided FE MRI acquisition is applied in the phase-encoding direction.

19. The method of any preceding embodiment, wherein the one-sided FE MRI acquisition is applied in one or more of the frequency-encoding direction and slice-encoding direction.

21. The method of any preceding embodiment, the method further comprising: performing FE MRI acquisition in a third direction of the MRI scanner; wherein one-sided FE MRI acquisition is applied both the frequency-encoding direction and slice-encoding direction.

22. The method of any preceding embodiment, wherein two-sided FE MRI acquisition of the target anatomy is performed in a y-direction associated with the MRI scanner and one-sided FE MRI acquisition is performed in an x-direction associated with the MRI scanner, the method further comprising: performing one-sided or two-sided FE MRI acquisition in a z direction.

23. The method of any preceding embodiment, wherein interleaved, two-sided FE MRI acquisition comprises alternating a polarity of a FE gradient between successive cardiac phases.

24. The method of any preceding embodiment, the method further comprising: calculating a flow-compensated (FC) background phase from the FE datasets.

25. The method of any preceding embodiment, wherein flow compensated background phase is calculated according to the equation:

$$\Phi_{FC,n} = \underset{\Phi_{FC,n}}{\operatorname{argmin}} \left\| \vec{V_n} \cdot \vec{V_{n+1}} \right| - |\vec{V_n}| * |\vec{V_{n+1}}| \right\|; \text{ wherein}$$

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}); \text{ wherein}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n});$$

and wherein $\phi_{FEz,n}$ are acquired FE phase signals for cardiac phase n in x, y and z directions, respectively, $\phi_{FEx,n+1}$, $\phi_{FEy,n+1}$ and $\phi_{FEz,n+1}$ are the acquired FE phase signals for cardiac phase n+1 in the x, y and z directions, respectively, and $\vec{V_n}$ and $|\vec{V_{n+1}}|$ are the velocity magnitudes for cardiac phases n and n+1, respectively.

26. The method of any preceding embodiment, the method further comprising: measuring one or more physiological characteristics of the target anatomy from the FE datasets.

27. The method of any preceding embodiment: wherein the one or more physiological characteristics of the target anatomy comprises calculating 3-D blood velocities of the target anatomy; wherein the 3-D blood velocities are calculated by subtracting the FC background phase from the time-resolved FE datasets.

28. The method of any preceding embodiment, the method further comprising: generating 4D flow data as a function of the calculated FC background phase and the time-resolved FE datasets.

29. A system for time-resolved PC-MRI of a target anatomy, the system comprising: (a) an MRI scanner configured for scanning the target anatomy; (b) a computer processor coupled to the MRI scanner; and (c) a non-transitory computer-readable memory storing instructions executable by the computer processor; (d) wherein said instructions, when executed by the computer processor, perform steps comprising: (i) performing one-sided flow-encoded (FE) MRI acquisition of the target anatomy in a first direction of three orthogonal directions associated with the MRI scanner; (ii) performing interleaved, two-sided FE MRI acquisition of the target anatomy in a second direction of the MRI scanner; and (iii) generating successive time-resolved FE datasets of the target anatomy from the one-sided FE MRI acquisition and interleaved, two-sided FE MRI acquisition.

30. The system of any preceding embodiment: wherein the three orthogonal directions comprise a phase-encoding direction, a frequency-encoding direction and a slice-encoding direction; and wherein the interleaved, two-sided FE MRI acquisition is applied in the phase-encoding direction.

31. The system of any preceding embodiment, wherein the one-sided FE MRI acquisition is applied in one or more of the frequency-encoding direction and slice-encoding direction.

32. The system of any preceding embodiment, wherein said instructions when executed by the computer processor further perform steps comprising: performing FE MRI acquisition in a third direction of the MRI scanner; and wherein one-sided FE MRI acquisition is applied both the frequency-encoding direction and slice-encoding direction.

33. The system of any preceding embodiment, wherein two-sided FE MRI acquisition of the target anatomy is performed in a y-direction associated with the MRI scanner and a one-sided FE MRI acquisition is performed in an x-direction associated with the MRI scanner, wherein said instructions when executed by the computer processor further perform steps comprising: performing a one-sided or two-sided FE MRI acquisition in a z direction.

34. The system of any preceding embodiment, wherein interleaved, two-sided FE MRI acquisition comprises alternating a polarity of a FE gradient between successive cardiac phases.

35. The system of any preceding embodiment, wherein said instructions when executed by the computer processor further perform steps comprising: (iv) calculating a flow-compensated (FC) background phase from the FE datasets.

36. The system of any preceding embodiment, wherein flow compensated background phase is calculated according to the equation:

$$\Phi_{FC,n} = \underset{\Phi_{FC,n}}{\operatorname{argmin}} \left\| \vec{V_n} \cdot \vec{V_{n+1}} \right| - |\vec{V_n}| * |\vec{V_{n+1}}| \right\|; \text{ wherein}$$

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}); \text{ wherein}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n});$$

and wherein $\phi_{FEz,n}$ are acquired FE phase signals for cardiac phase n in x, y and z directions, respectively, $\phi_{FEx,n+1}$, $\phi_{FEy,n+1}$ and $\phi_{FEz,n+1}$ are the acquired FE phase signals for cardiac phase n+1 in the x, y and z directions, respectively, and $|\vec{V_n}|$ and $|\vec{V_{n+1}}|$ are the velocity magnitudes for cardiac phases n and n+1, respectively.

37. The system of any preceding embodiment, wherein said instructions when executed by the computer processor further perform steps comprising: measuring one or more physiological characteristics of the target anatomy from the FE datasets.

38. The system of any preceding embodiment: wherein the one or more physiological characteristics of the target anatomy comprises calculating 3-D blood velocities of the target anatomy; wherein the 3-D blood velocities are calculated by subtracting the FC background phase from the time-resolved FE datasets.

39. The system of any preceding embodiment, wherein said instructions when executed by the computer processor further perform steps comprising: generating 4D flow data as a function of the calculated FC background phase and the time-resolved FE datasets.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

RMSE of FC calculation (radian) as function of $SNR^{-1}$ and 1-VR

| | 1-VR | | | | |
|---|---|---|---|---|---|
| $SNR^{-1}$ | 0.1 | 0.25 | 0.5 | 0.75 | 0.9 |
| 0.02(FEO) | 0.199 | 0.076 | 0.036 | 0.023 | 0.019 |
| 0.02(HOTFEO) | 0.016 | 0.015 | 0.013 | 0.012 | 0.011 |
| 0.025(FEO) | 0.252 | 0.094 | 0.044 | 0.028 | 0.024 |
| 0.025(HOTFEO) | 0.020 | 0.019 | 0.017 | 0.015 | 0.014 |
| 0.033(FEO) | 0.359 | 0.124 | 0.058 | 0.038 | 0.032 |
| 0.033(HOTFEO) | 0.026 | 0.025 | 0.022 | 0.020 | 0.019 |
| 0.05(FEO) | 0.534 | 0.186 | 0.086 | 0.056 | 0.048 |
| 0.05(HOTFEO) | 0.039 | 0.037 | 0.032 | 0.029 | 0.028 |

What is claimed is:

1. An apparatus for time-resolved PC-MRI of a target anatomy, the system comprising:
  (a) a computer processor; and
  (b) a non-transitory computer-readable memory storing instructions executable by the computer processor;
  (c) wherein said instructions, when executed by the computer processor, perform steps comprising:
    (i) performing one-sided flow-encoded (FE) MRI acquisition of the target anatomy in a first direction of three orthogonal directions associated with an MRI scanner;
    (ii) performing interleaved, two-sided FE MRI acquisition of the target anatomy in a second direction of the MRI scanner; and
    (iii) generating successive time-resolved FE datasets of the target anatomy from the one-sided FE MRI acquisition and interleaved, two-sided FE MRI acquisition.

2. The apparatus of claim 1:
  wherein the three orthogonal directions comprise a phase-encoding direction, a frequency-encoding direction and a slice-encoding direction of the scanner; and
  wherein the interleaved, two-sided FE MRI acquisition is applied in the phase-encoding direction.

3. The apparatus of claim 2, wherein the one-sided FE MRI acquisition is applied in one or more of the frequency-encoding direction and slice-encoding direction.

4. The apparatus of claim 2, wherein said instructions when executed by the computer processor further perform steps comprising:
  performing FE MRI acquisition in a third direction of the MRI scanner;
  wherein one-sided FE MRI acquisition is applied both the frequency-encoding direction and slice-encoding direction.

5. The apparatus of claim 1:
  wherein two-sided FE MRI acquisition of the target anatomy is performed in a y-direction associated with the MRI scanner and one-sided FE MRI acquisition is performed in an x-direction associated with the MRI scanner; and
  wherein said instructions when executed by the computer processor further perform steps comprising:
  performing one-sided or two-sided FE MRI acquisition in a z direction.

6. The apparatus of claim 1, wherein interleaved, two-sided FE MRI acquisition comprises alternating a polarity of a FE gradient between successive cardiac phases.

7. The apparatus of claim 1, wherein said instructions when executed by the computer processor further perform steps comprising:

(iv) calculating a flow-compensated (FC) background phase from the FE datasets.

8. The apparatus of claim 7, wherein flow compensated background phase is calculated according to the equation:

$$\Phi_{FC,n} = \underset{\Phi_{FC,n}}{\operatorname{argmin}} \left| |\vec{V_n} \cdot \vec{V_{n+1}}| - |\vec{V_n}| * |\vec{V_{n+1}}| \right|; \text{ wherein}$$

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}); \text{ wherein}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n});$$

and wherein $\Phi_{Fez,n}$ are acquired FE phase signals for cardiac phase n in x, y and z directions, respectively, $\Phi_{FEx,n+1}$, $\Phi_{FEy,n+1}$ and $\Phi_{FEz,n+1}$ are the acquired FE phase signals for cardiac phase n+1 in the x, y and z directions, respectively, $\vec{V_n}$ and $|\vec{V_{n+1}}|$ are the velocity magnitudes for cardiac phases n and n+1, respectively.

9. The apparatus of claim 7 wherein said instructions when executed by the computer processor further perform steps comprising:
measuring one or more physiological characteristics of the target anatomy from the FE datasets;
wherein the one or more physiological characteristics of the target anatomy comprises calculating 3-D blood velocities of the target anatomy; and
wherein the 3-D blood velocities are calculated by subtracting the FC background phase from the time-resolved FE datasets.

10. The apparatus of claim 7, wherein said instructions when executed by the computer processor further perform steps comprising:
generating 4D flow data as a function of the calculated FC background phase and the time-resolved FE datasets.

11. The system of claim 1 further comprising an MRI scanner configured for scanning the target anatomy and wherein the computer processor is coupled to the MRI scanner to control operation of the MRI scanner.

12. A method for time-resolved, three-dimensional PC-MRI of a target anatomy, the method comprising:
performing one-sided flow-encoded (FE) MRI acquisition of the target anatomy in a first direction of three orthogonal directions associated with an MRI scanner;
performing interleaved, two-sided FE MRI acquisition of the target anatomy in a second direction of the MRI scanner; and
outputting successive time-resolved FE datasets of the target anatomy from the one-sided FE MRI acquisition and interleaved, two-sided FE MRI acquisition.

13. The method of claim 12:
wherein the three orthogonal directions comprise a phase-encoding direction, a frequency-encoding direction and a slice-encoding direction of the scanner; and
wherein the interleaved, two-sided FE MRI acquisition is applied in the phase-encoding direction.

14. The method of claim 13, wherein the one-sided FE MRI acquisition is applied in one or more of the frequency-encoding direction and slice-encoding direction.

15. The method of claim 13, the method further comprising:
performing FE MRI acquisition in a third direction of the MRI scanner; wherein one-sided FE MRI acquisition is applied both the frequency-encoding direction and slice-encoding direction.

16. The method of claim 12, wherein two-sided FE MRI acquisition of the target anatomy is performed in a y-direction associated with the MRI scanner and one-sided FE MRI acquisition is performed in an x-direction associated with the MRI scanner, the method further comprising:
performing one-sided or two-sided FE MRI acquisition in a z direction.

17. The method of claim 12, wherein interleaved, two-sided FE MRI acquisition comprises alternating a polarity of a FE gradient between successive cardiac phases.

18. The method of claim 12, the method further comprising:
calculating a flow-compensated (FC) background phase from the FE datasets.

19. The method of claim 18, wherein flow compensated background phase is calculated according to the equation:

$$\Phi_{FC,n} = \underset{\Phi_{FC,n}}{\operatorname{argmin}} \left| |\vec{V_n} \cdot \vec{V_{n+1}}| - |\vec{V_n}| * |\vec{V_{n+1}}| \right|; \text{ wherein}$$

$$\vec{V_n} = \frac{VENC}{\pi} * (\Phi_{FEx,n} - \Phi_{FC,n}, \Phi_{FEy,n} - \Phi_{FC,n}, \Phi_{FEz,n} - \Phi_{FC,n}); \text{ wherein}$$

$$\vec{V_{n+1}} = \frac{VENC}{\pi} * (\Phi_{FEx,n+1} - \Phi_{FC,n}, \Phi_{FEy,n+1} - \Phi_{FC,n}, \Phi_{FEz,n+1} - \Phi_{FC,n});$$

and wherein $\Phi_{FEz,n}$ are acquired FE phase signals for cardiac phase n in x, y and z directions, respectively, $\Phi_{FEx,n+1}$, $\Phi_{FEy,n+1}$ and $\Phi_{FEz,n+1}$ are the acquired FE phase signals for cardiac phase n+1 in the x, y and z directions, respectively, and $\vec{V_n}$ and $|\vec{V_{n+1}}|$ are the velocity magnitudes for cardiac phases n and n+1, respectively.

20. The method of claim 18 the method further comprising:
measuring one or more physiological characterisitics of the target anatomy from the FE datasets;
wherein the one or more physiological characteristics of the target anatomy comprises calculating 3-D blood velocities of the target anatomy; and
wherein the 3-D blood velocities are calculated by subtracting the FC background phase from the time-resolved FE datasets.

* * * * *